US00PP13060P2

(12) United States Plant Patent
Ilsink

(10) Patent No.: US PP13,060 P2
(45) Date of Patent: Oct. 8, 2002

(54) FLORIBUNDA ROSE PLANT NAMED 'INTERTRODAN'

(75) Inventor: Peter Ilsink, Leersum (NL)

(73) Assignee: Interplant B.V. International Plant and Trading Company, Leersum (NL)

( * ) Notice: Subject to any disclaimer, the term of this patent is extended or adjusted under 35 U.S.C. 154(b) by 0 days.

(21) Appl. No.: 09/739,533

(22) Filed: Dec. 13, 2000

(51) Int. Cl.[7] ..... A01H 5/00

(52) U.S. Cl. ..... Plt./144

(58) Field of Search ..... Plt./144, 141, 130, Plt./133

*Primary Examiner*—Bruce R. Campell
*Assistant Examiner*—June Hwu
(74) *Attorney, Agent, or Firm*—Klarquist Sparkman, LLP

(57) ABSTRACT

Floribunda rose plant having excellent production of cut flower spray roses; long stem length; good vase life; few thorns; and ease of propagation as a budded plant or as a rooted cutting.

1 Drawing Sheet

LATIN NAME OF THE GENUS AND SPECIES OF THE PLANT

*Rosa hybrida.*

VARIETY DENOMINATION

'Intertrodan'.

BACKGROUND OF THE INVENTION

The present invention relates to a new and distinct variety of rose plant of the floribunda class which was originated by me by crossing an unnamed seedling, (INTERlis×unnamed seedling) with an unnamed seedling (unnamed seedling× unnamed seedling). INTERlis is patented (U.S. Plant Pat. No. 9,722).

The primary objective of this breeding was to produce a new rose variety having a white spray rose for the cut flower market that has good production, good stem length and good vase life.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Excellent production of cut flower spray roses;
2. Long stem length
3. Good vase life;
4. Few thorns; and
5. Ease of propagation as a budded plant or as a rooted cutting.

Plants of this variety produce clusters of flowers at the top of the stems, a plant producing in a greenouse about 25 to 27 stems per year.

Asexual reproduction of this new variety by cutting and budding, as performed at Wasco and Somis, Calif., shows that the foregoing and all other characteristics and distinctions come true to form and are established and transmitted through succeeding propagations.

BRIEF DESCRIPTION OF THE DRAWING

The accompanying illustration shows typical specimens of the vegetative growth and flowers of this new variety in different stages of development, depicted in color as nearly true as it is resonably possible to make the same in a color illustration of this character.

DETAILED BOTANICAL DESCRIPTION

The following is a detailed description of my new rose cultivar with color descriptions using terminology in accordance with The Royal Horticultural Society (London) colour chart, except where ordinary dictionary significance of color is indicated. The observed plant is seven months old.

Parentage:

*Seed parent.*—Unnamed seedling (INTERlis×unnamed seedling).

*Pollen parent.*—Unnamed seedling (Unnamed seedling×unnamed seedling).

Classification:

*Botanical.*—*Rosa hybrida.*

*Commercial.*—Floribunda.

FLOWER

Observations made from specimens grown in a greenhouse environment at Somis, Calif. in March, 1999–October, 2000.

Blooming habit: Continuous.

Bud:

*Size.*—About ¾" to ⅞" long when the petals start to unfurl.

*Form.*—The bud form is long, pointed ovoid.

*Color.*—When sepals first divide, bud color is Yellow-White Group 158D. When half blown, the upper sides of the petals are White Group 155D; and the lower sides of the petals are Yellow-White Group 158D.

*Sepals.*—Color: Green Group 138B. Size: Average size 25 mm. Surface texture: Upper surface smooth. Inner surface smooth with fine hairs. There are three lightly appendaged sepals. There are two unappendaged sepals with hairy edges.

*Receptacle.*—Color: Yellow-Green Group 146B. Shape: Funnel. Size: Small, about 5/16×1/4 inches. Surface: Smooth.

*Peduncle.*—Length: Variable, one spray of flower, range 7 cm to 15.5 cm. Surface: Glandular. Color: Yellow-Gren Group 146A. Strength: Stiff, erect, and slender. Foliaceous Appendages: Average length 7 mm to 9 mm; color at base — Orange-Red Group 33A, color at outer portion — Green Group 141A.

*Pedicel.*—Length: Variable, one spray of flower, range 3.5 cm to 9 cm.

Bloom:

*Size.*—Small. Average open diameter is 2½ inches.

*Borne.*—Several together in rounded to flat clusters of five to twelve blooms.

*Stems.*—Strength: Strong. Average length is about 26–30 inches.

*Form.*—When first open: High centered. Permanence: Flattens, all petals curl quill fashion.

*Petalage.*—Number of petals under normal conditions: 40–50.

*Shape.*—Margin: Entire, reflexed. Base: Ovid. Apex: Pointed.

*Color.*—The upper sides of the petals are White Group 155D. The reverse sides of the petals are White Group 155D. The base of each petal has, on both surfaces, a small 1/16"×1/16" Yellow-White Group 158D color spot. The major color on the upper side is White Group 155D.

*Variegations.*—Occassional Yellow-Green Group 146D streaks on the guard petals.

*Discoloration.*—The general tonality at the end of the first day: No change. No change through day ten in the vase.

*Fragrance.*—None.

Petals:

*Texture.*—Thick, leathery.

*Shape.*—Deltoid.

*Form.*—Tips slightly recurved, edges slightly quilled.

*Arrangement.*—Imbricated. Petaloids in the center are few (2–5) and small (1/8"–1/4" wide×1/4"–1/2" long), and are White Group 155D.

*Persistence.*—Petals drop off cleanly before drying.

*Lastingness.*—On the plant: Long (about 7–8 days). As a cut flower: Long (about 10–12 days).

Reproductive parts:

*Anthers.*—Size: Medium; average size 2 mm. Quantity: Many; average number 72. Color: Yellow-Orange Group 19C. Arrangement: Regular around styles.

*Filaments.*—Color: Yellow Group 3D; average size 6 mm.

*Pollen.*—Color: Greyed-Orange Group 165C.

*Styles.*—Color: Green-White Group 157A; average size 8 mm; average number — 41.

*Stigmas.*—Color: Yellow-White Group 158A.

*Hips/seeds.*—None observed in seven month old plants.

Plant:

*Form.*—Bush.

*Growth.*—Vigorous, upright, and branching. At maturity (after one year in a greenhouse), height is 4–6 feet, width is 2–3 feet.

Foliage: Number of leaflets on normal mid-stem leaves: 5.

*Size.*—Medium (6" long×5" wide).

*Quantity.*—Abundant.

*Color.*—New foliage: Upper surface: Greyed-Orange Group 175C. Lower surface: Greyed-Orange Group 17C (both sides quickly become green). Old foliage: Upper surface: Green Group 139A. Lower surface: Green Group 138A.

Leaflets:

*Shape.*—Pointed oval.

*Size.*—Upper leaflet: Terminal length 65 mm; Terminal width 40 mm. Lower leaflet: Terminal length 48 mm; Terminal width 26 mm.

*Texture.*—Upper surface: Leathery and glossy. Under surface: Somewhat rough, dull.

*Edge.*—Serrated.

*Serration.*—Single and small.

*Petiole rachis.*—Color: Green Group 138A.

*Petiole underside.*—Smooth.

*Stipules.*—Medium and serrated (about ½ inch).

*Disease resistance.*—Resistant to mildew and rust, susceptible to blackspot under normal growing conditions.

Wood:

*New wood.*—Color: Greyed-Orange Group 175C. Bark: Smooth.

*Old wood.*—Color: Green Group 137C. Bark: Smooth.

Prickles:

*Quantity.*—On old growth main canes from base: Few. One such prickle measured 6 mm. On old growth laterals from main canes: Few. One such prickle measured 6 mm.

*Form.*—Medium, hooked downward.

*Color when young.*—Greyed-Purple Group 183C.

*Color when mature.*—Greyed-Orange Group 174A.

Small prickles:

*Quantity.*—On main stalks: None observed. On laterals: None observed.

I claim:

1. A new and distinct variety of rose plant of the floribunda class, substantially as herein shown and described, characterized particularly by its excellent production of cut flower spray roses; long stem length; good vase life; few thorns; and ease of progagation as a budded plant or as a rooted cutting.

* * * * *

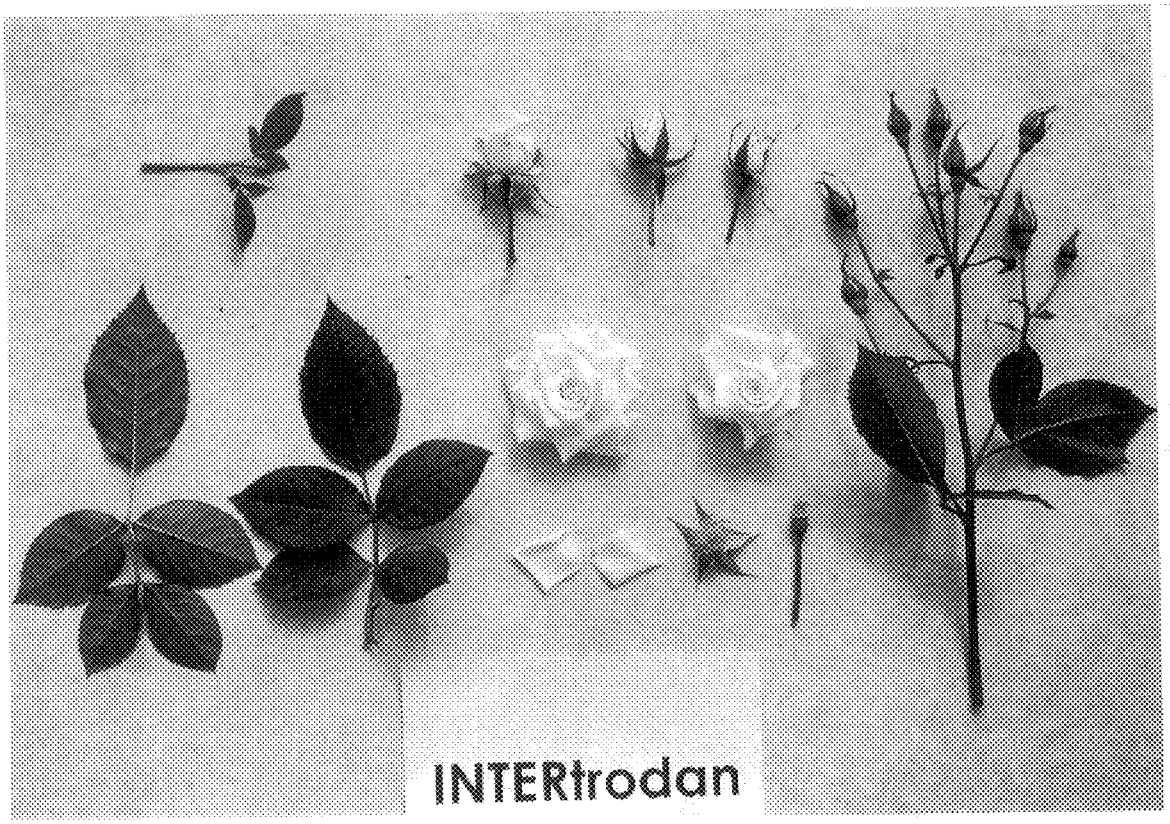
INTERtrodan